US011529104B2

(12) United States Patent
Balabine et al.

(10) Patent No.: US 11,529,104 B2
(45) Date of Patent: Dec. 20, 2022

(54) METHOD OF BLOOD PRESSURE ESTIMATION USING TREND ANALYSIS

(71) Applicant: AiCare Corporation, San Jose, CA (US)

(72) Inventors: Helen Balabine, Menlo Park, CA (US); Sean Tan, San Jose, CA (US); John Fee, Garland, TX (US)

(73) Assignee: AI CARE CORPORATION, San Jose, CA (US)

( * ) Notice: Subject to any disclaimer, the term of this patent is extended or adjusted under 35 U.S.C. 154(b) by 366 days.

(21) Appl. No.: 16/180,109

(22) Filed: Nov. 5, 2018

(65) Prior Publication Data

US 2019/0142346 A1    May 16, 2019

Related U.S. Application Data

(60) Provisional application No. 62/585,258, filed on Nov. 13, 2017.

(51) Int. Cl.
*A61B 5/00* (2006.01)
*A61B 5/021* (2006.01)
(Continued)

(52) U.S. Cl.
CPC .......... *A61B 5/7275* (2013.01); *A61B 5/0022* (2013.01); *A61B 5/0059* (2013.01);
(Continued)

(58) Field of Classification Search
CPC ... A61B 5/7275; A61B 5/02108; A61B 5/681; A61B 5/021; A61B 5/0059;
(Continued)

(56) References Cited

U.S. PATENT DOCUMENTS 4,928,702 A * 5/1990 Cousin .................. G01L 9/0076
600/491
5,935,077 A * 8/1999 Ogle .................... A61B 5/0265
600/504

(Continued)

FOREIGN PATENT DOCUMENTS

| CN | 204618206 U | 9/2015 |
| WO | 0213158 A1 | 2/2002 |
| WO | 2017086071 | 5/2017 |

OTHER PUBLICATIONS

International Search Report and Written Opinion, PCT/US2018/059313 (ISA/KR) dated Mar. 6, 2019.

*Primary Examiner* — Devin B Henson
*Assistant Examiner* — Justin Xu
(74) *Attorney, Agent, or Firm* — Edwin S. Flores; Daniel J. Chalker; Chalker Flores LLP

(57) ABSTRACT

The present invention includes an apparatus and method for blood pressure trend determination of a subject comprising: a housing; at least one of a photoplethysmographic (PPG) sensor or a magnetic sensor in or on the housing and adapted to be worn by the subject, wherein the PPG/magnetic sensor uses a pulse oximeter to measure changes in skin light absorption; a processor for receiving a signal from the at least one of the PPG sensor or the magnetic sensor measurements, wherein the processor comprises a non-transitory computer readable medium having instruction stored thereon, wherein the instructions, when executed by the processor, cause the processor to: measure a trend analysis results to determine the blood pressure trend over a time period; and an input/output device that at least one of stores, displays, or transmits blood pressure trend of the subject.

30 Claims, 8 Drawing Sheets

(51) Int. Cl.
 *A61B 5/024* (2006.01)
 *G16H 40/67* (2018.01)
 *G16H 50/30* (2018.01)

(52) U.S. Cl.
 CPC .......... *A61B 5/021* (2013.01); *A61B 5/02108* (2013.01); *A61B 5/02438* (2013.01); *A61B 5/681* (2013.01); *A61B 5/7203* (2013.01); *A61B 5/02416* (2013.01); *A61B 2562/0223* (2013.01)

(58) Field of Classification Search
 CPC . A61B 5/0022; A61B 5/02438; A61B 5/7203; A61B 5/02416; A61B 2562/0223; G16H 40/67; G16H 50/30
 See application file for complete search history.

(56) References Cited

U.S. PATENT DOCUMENTS

| | | | |
|---|---|---|---|
| 6,017,313 A * | 1/2000 | Bratteli | A61B 5/021 600/481 |
| 9,649,054 B2 | 5/2017 | Lamego et al. | |
| 9,668,656 B2 | 6/2017 | Banet et al. | |
| 2002/0095424 A1 | 7/2002 | Chung | |
| 2004/0111293 A1 | 6/2004 | Firanek et al. | |
| 2007/0156055 A1* | 7/2007 | Royalty | A61B 5/1126 600/509 |
| 2008/0081961 A1* | 4/2008 | Westbrook | A61B 5/412 600/301 |
| 2012/0059267 A1 | 3/2012 | Lamego et al. | |
| 2013/0079656 A1* | 3/2013 | Dripps | A61B 5/14551 600/529 |
| 2014/0083867 A1* | 3/2014 | Schaible | G16H 50/20 205/782 |
| 2015/0065826 A1 | 3/2015 | Mulligan et al. | |
| 2015/0366516 A1 | 12/2015 | Dripps et al. | |
| 2016/0073914 A1* | 3/2016 | Lapetina | A61B 5/282 600/384 |
| 2016/0296157 A1* | 10/2016 | Girouard | G16H 40/67 |
| 2017/0238819 A1 | 8/2017 | Waller et al. | |
| 2019/0180636 A1* | 6/2019 | Lei | G06F 16/90332 |

* cited by examiner

METHOD OF BLOOD PRESSURE ESTIMATION USING TREND ANALYSIS

CROSS-REFERENCE TO RELATED APPLICATIONS

This application claims priority to U.S. Provisional Application Ser. No. 62/585,258, filed Nov. 13, 2017, the entire contents of which are incorporated herein by reference.

STATEMENT OF FEDERALLY FUNDED RESEARCH

None.

TECHNICAL FIELD OF THE INVENTION

The present invention relates in general to the field of blood pressure determination, and more particularly to novel devices and methods of blood pressure estimation using trend analysis.

BACKGROUND OF THE INVENTION

Without limiting the scope of the invention, its background is described in connection with blood pressure measurements.

One such invention is taught in U.S. Pat. No. 9,668,656, issued to Banet, et al., is entitled "Body-worn system for measuring continuous non-invasive blood pressure (cNIBP)". Briefly, these inventors are said to teach a technique for continuous measurement of blood pressure based on pulse transit time and which does not require any external calibration. This technique is carried out with a body-worn monitor that measures blood pressure and other vital signs, and wirelessly transmits them to a remote monitor. A network of body-worn sensors, typically placed on the patient's right arm and chest, connect to the body-worn monitor and measure time-dependent ECG, PPG, accelerometer, and pressure waveforms. The disposable sensors can include a cuff that features an inflatable bladder coupled to a pressure sensor, three or more electrical sensors (e.g. electrodes), three or more accelerometers, a temperature sensor, and an optical sensor (e.g., a light source and photodiode) attached to the patient's thumb.

Another such invention is taught in U.S. Pat. No. 9,649,054, issued to Lamego, et al., and is entitled "Blood pressure measurement method". Briefly, these inventors are said to teach a blood pressure measurement system that non-invasively determines an individual's blood pressure and that can include a noninvasive blood pressure sensor having an optical sensor and a motion sensor. The optical sensor can provide a photoplethysmograph signal obtained from a patient to a processor. A motion sensor can provide a motion signal to the processor responsive to motion of the patient. In one embodiment, the processor calculates or estimates the blood pressure of the patient based on the photoplethysmograph signal and the motion signal. It is also said that the system can obtain this blood pressure measurement without an occlusive cuff, thereby reducing patient discomfort. In other implementations, the processor is said to calculate a blood pressure-related parameter from the photoplethysmograph and motion signal, wherein the processor can occasionally trigger an occlusive cuff measurement as this parameter changes, thereby reducing the frequency of occlusive cuff measurements.

SUMMARY OF THE INVENTION

In one embodiment, the present invention includes an apparatus for blood pressure trend determination of a subject comprising: a housing; at least one of a photoplethysmographic (PPG) sensor or a magnetic sensor in or on the housing and adapted to be worn by the subject, wherein the PPG/magnetic sensor uses a pulse oximeter to measure changes in skin light absorption; a processor for receiving a signal from the at least one of the PPG sensor or the magnetic sensor measurements, wherein the processor comprises a non-transitory computer readable medium having instruction stored thereon, wherein the instructions, when executed by the processor, cause the processor to: receive the PPG/magnetic sensor measurements over a first time interval; identify a second time interval within the first time interval with statistically stable measurements; identify within the second time interval a sequence of time intervals containing an optimal number of systolic and diastolic cardiac periods (SCP, DCP) suitable for blood pressure trend computation; apply a statistical analysis to determining the optimal sequence of time intervals; eliminate a noise in the sequence of time intervals by applying an adaptive or fixed low-pass Fourier filter to each element of the sequence; compute a trend of systolic blood pressure by finding slope of a best-fit line traversing systolic blood pressure measurement peaks; compute trend of diastolic blood pressure by finding slope of a best-fit line traversing diastolic blood pressure measurement troughs and inverting the slope sign; and combine the trend analysis results to determine the blood pressure trend over a time period; and an input/output device that at least one of stores, displays, or transmits blood pressure trend of the subject. In one aspect, the processor receives blood pressure measurements obtained from using a pressure cuff and the PPG/magnetic sensor at the same time, and calibrates the PPG/magnetic sensor to match the pressure cuff measurements. In another aspect, the processor further uses PPG measurements to compute trends of systolic and diastolic blood pressure change. In another aspect, the processor further uses an initial blood pressure measurement and computed trends to determine blood pressure for the duration of PPG measurements. In another aspect, the statistical analysis is a chi-squared and goodness-of-fit analysis. In another aspect, the input/output device is a wireless communication is selected from at least one of: IEEE 802.11 (WiFi), IEEE 802.15.4, BLUETOOTH protocol, Near Field Communication (NFC), Radio Frequency Identification (RFID), SIGFOX protocol, WiMax (world interoperability for microwave access), Universal Mobile Telecommunications System (UMTS), 3GPP Long Term Evolution (LTE), IMS, High Speed Packet Access (HSPA), Global System for Mobile communication (GSM), 3G, 4G, 5G, 6G and higher, AM, or FM. In another aspect, the input/output device connects to a network selected from Zigbee, Bluetooth, WiMax (WiMAX Forum Protocol), Wi-Fi (Wi-Fi Alliance Protocol), GSM (Global System for Mobile Communication), PCS (Personal Communications Services protocol), D-AMPS (Digital-Advanced Mobile Phone Service Protocol), 6LoWPAN (IPv6 Over Low Power Wireless Personal Area Networks Protocol), ANT (ANT network protocol), ANT+, Z-Wave, DASH7 (DASH7 Alliance Protocol), EnOcean, INSTEON, NeuRF ON, Senceive, WirelessHART (Wireless Highway Addressable Remote Transducer Protocol), Contiki, TinyOS (Tiny OS Alliance Protocol), GPRS (General Packet Radio Service), TCP/IP (Transmission Control Protocol and Internet Protocol), CoAP (Constrained Application Protocol), MQTT (Message Queuing Telemetry Transport), TR-50 (Engineering Committee TR-50 Protocol, OMA LW M2M (Open Mobile Alliance LightWeight machine-to-machine Protocol), and ETSIM2M (European Telecommunication Standards Institute machine-to-machine Protocol), Bluetooth Low Energy (BLE), minimal energy Bluetooth signal, Infrared Data Association (IrDA) protocols, and standards related to any of the foregoing. In another aspect, the input/output device is connected physically to the apparatus via a Universal Serial Bus (USB) interface standard, a Compact Flash (CF) interface standard, a MultiMediaCard (MMC) interface standard, an embedded MMC (eMMC) interface standard, a Thunderbolt interface standard, a UFS interface standard, a Secure Digital (SD) interface standard, a Memory Stick interface standard, an xD-picture card interface standard, an Integrated Drive Electronics (IDE) interface standard, a Serial Advanced Technology Attachment (SATA) interface standard, an external SATA (eSATA) interface standard, a Small Computer System Interface (SCSI) interface standard, a Serial Attached Small Computer System Interface (SAS) interface standard, a Fibre Channel interface standard, an Ethernet interface standard, Peripheral Component Interconnect (PCI), Infiniband, or Firewire. In another aspect, the input/output device communicates with a local network that is connected to a global telecommunications network to store or transmit information through the cloud. In another aspect, the magnetic sensor detects pulse induced body movement that affects the magnetic field to measure a blood flow. In another aspect, an output from the magnetic sensor is used to determine a magnetocardiogram (MCG) and a cardiac cycle. In another aspect, the processor further calculates an absolute blood pressure locally at the magnetic sensor. In another aspect, the processor distinguishes between the magnetic field caused by the blood flow and a skin movement that disturbs the electromagnetic field or correlates skin movement to blood flow. In another aspect, the processor further comprises a feedback and monitoring algorithm that calculates that a goodness-of-fit (GOF) is >0.9.

In one embodiment, the present invention includes a method of blood pressure trend determination of a subject comprising: providing a device comprising at least one of a photoplethysmographic (PPG) sensor or a magnetic sensor to the subject, wherein the PPG/magnetic sensor uses a pulse oximeter to measure changes in skin light absorption; transmitting results of the PPG/magnetic sensor measurements to a processor, wherein the processor comprises a non-transitory computer readable medium having instruction stored thereon, wherein the instructions, when executed by the processor, cause the processor to: receive the PPG/magnetic sensor measurements over a first time interval; identify a second time interval within the first time interval with statistically stable measurements; identify within the second time interval a sequence of time intervals containing an optimal number of systolic and diastolic cardiac periods (SCP, DCP) suitable for blood pressure trend computation; apply a statistical analysis to determining the optimal sequence of time intervals; eliminate a noise in the sequence of time intervals by applying an adaptive or fixed low-pass Fourier filter to each element of the sequence; compute a trend of systolic blood pressure by finding slope of a best-fit line traversing systolic blood pressure measurement peaks; compute trend of diastolic blood pressure by finding slope of a best-fit line traversing diastolic blood pressure measurement troughs and inverting the slope sign; and combine the trend analysis results to determine the blood pressure trend over a time period; and providing an input/output device that at least one of stores, displays, or transmits blood pressure trend of the subject. In one aspect, the method further comprises taking blood pressure measurement using a standard methodology and starting PPG sensor measurement at the same time. In another aspect, the method further comprises using PPG measurements to compute trends of systolic and diastolic blood pressure change. In another aspect, the method further comprises using an initial blood pressure measurement and computed trends to determine blood pressure for the duration of PPG measurements. In another aspect, the method further comprises using a statistical analysis that is a chi-squared and goodness-of-fit analysis. In another aspect, the input/output device is a wireless communication is selected from at least one of: IEEE 802.11 (WiFi), IEEE 802.15.4, BLUETOOTH protocol, Near Field Communication (NFC), Radio Frequency Identification (RFID), SIGFOX protocol, WiMax (world interoperability for microwave access), Universal Mobile Telecommunications System (UMTS), 3GPP Long Term Evolution (LTE), IMS, High Speed Packet Access (HSPA), Global System for Mobile communication (GSM), 3G, 4G, 5G, 6G and higher, AM, or FM. In another aspect, the input/output device connects to a network selected from Zigbee, Bluetooth, WiMax (WiMAX Forum Protocol), Wi-Fi (Wi-Fi Alliance Protocol), GSM (Global System for Mobile Communication), PCS (Personal Communications Services protocol), D-AMPS (Digital-Advanced Mobile Phone Service Protocol), 6LoWPAN (IPv6 Over Low Power Wireless Personal Area Networks Protocol), ANT (ANT network protocol), ANT+, Z-Wave, DASH7 (DASH7 Alliance Protocol), EnOcean, INSTEON, NeuRF ON, Senceive, WirelessHART (Wireless Highway Addressable Remote Transducer Protocol), Contiki, TinyOS (Tiny OS Alliance Protocol), GPRS (General Packet Radio Service), TCP/IP (Transmission Control Protocol and Internet Protocol), CoAP (Constrained Application Protocol), MQTT (Message Queuing Telemetry Transport), TR-50 (Engineering Committee TR-50 Protocol, OMA LW M2M (Open Mobile Alliance LightWeight machine-to-machine Protocol), and ETSIM2M (European Telecommunication Standards Institute machine-to-machine Protocol), Bluetooth Low Energy (BLE), minimal energy Bluetooth signal, Infrared Data Association (IrDA) protocols, and standards related to any of the foregoing. In another aspect, the input/output device is connected physically to the apparatus via a Universal Serial Bus (USB) interface standard, a Compact Flash (CF) interface standard, a MultiMediaCard (MMC) interface standard, an embedded MMC (eMMC) interface standard, a Thunderbolt interface standard, a UFS interface standard, a Secure Digital (SD) interface standard, a Memory Stick interface standard, an xD-picture card interface standard, an Integrated Drive Electronics (IDE) interface standard, a Serial Advanced Technology Attachment (SATA) interface standard, an external SATA (eSATA) interface standard, a Small Computer System Interface (SCSI) interface standard, a Serial Attached Small Computer System Interface (SAS) interface standard, a Fibre Channel interface standard, an Ethernet interface standard, Peripheral Component Interconnect (PCI), Infiniband, or Firewire. In another aspect, the input/output device communicates with a local network that is connected to a global telecommunications network to store or transmit information through the cloud. In another aspect, the magnetic detector detects pulse induced body movement that affects the magnetic field to measure a blood flow. In another aspect, an output from the magnetic sensor is used to determine a magnetocardiogram (MCG) and a cardiac cycle. In another aspect, the processor further calculates an absolute blood pressure locally at the magnetic sensor. In another aspect, the processor distinguishes between the magnetic field caused by the blood flow and a skin movement that disturbs the electromagnetic field or correlates skin movement to blood flow. In another aspect, the processor further comprises a feedback and monitoring algorithm that calculates that a goodness-of-fit (GOF) is >0.9.

In one embodiment, the present invention includes a computer implemented method for obtaining a blood pressure trend from a subject, comprising: providing a device comprising at least one of a photoplethismographic (PPG) sensor or a magnetic sensor to the subject, wherein the PPG/magnetic sensor uses a pulse oximeter to measure changes in skin light absorption; transmitting results of the PPG/magnetic sensor measurements to a processor, wherein the processor comprises A non-transitory computer readable medium having instruction stored thereon, wherein the instructions, when executed by the processor, cause the processor to: receive the PPG/magnetic sensor measurements over a first time interval; identify a second time interval within the first time interval with statistically stable measurements; identify within the second time interval a sequence of time intervals containing an optimal number of systolic and diastolic cardiac periods (SCP, DCP) suitable for blood pressure trend computation; apply a statistical analysis to determining the optimal sequence of time intervals; eliminate a noise in the sequence of time intervals by applying an adaptive or fixed low-pass Fourier filter to each element of the sequence; compute a trend of systolic blood pressure by finding slope of a best-fit line traversing systolic blood pressure measurement peaks; compute trend of diastolic blood pressure by finding slope of a best-fit line traversing diastolic blood pressure measurement troughs and inverting the slope sign; and combine the trend analysis results to determine the blood pressure trend over a time period.

In one embodiment, the present invention includes a non-transitory computer readable medium for obtaining a blood pressure trend from a subject having instruction stored thereon, wherein the instructions, when executed by the processor, cause the processor to: receive the PPG/magnetic sensor measurements over a first time interval; identify a second time interval within the first time interval with statistically stable measurements; identify within the second time interval a sequence of time intervals containing an optimal number of systolic and diastolic cardiac periods (SCP, DCP) suitable for blood pressure trend computation; apply a statistical analysis to determine an optimal sequence of time intervals; eliminate a noise in the sequence of time intervals by applying an adaptive or fixed low-pass Fourier filter to each element of the sequence; compute a trend of systolic blood pressure by finding slope of a best-fit line traversing systolic blood pressure measurement peaks; compute trend of diastolic blood pressure by finding slope of a best-fit line traversing diastolic blood pressure measurement troughs and inverting the slope sign; and combine the trend analysis results to determine the blood pressure trend over a time period.

BRIEF DESCRIPTION OF THE DRAWINGS

For a more complete understanding of the features and advantages of the present invention, reference is now made to the detailed description of the invention along with the accompanying FIGS. and in which.

DETAILED DESCRIPTION OF THE INVENTION

Figure 1:
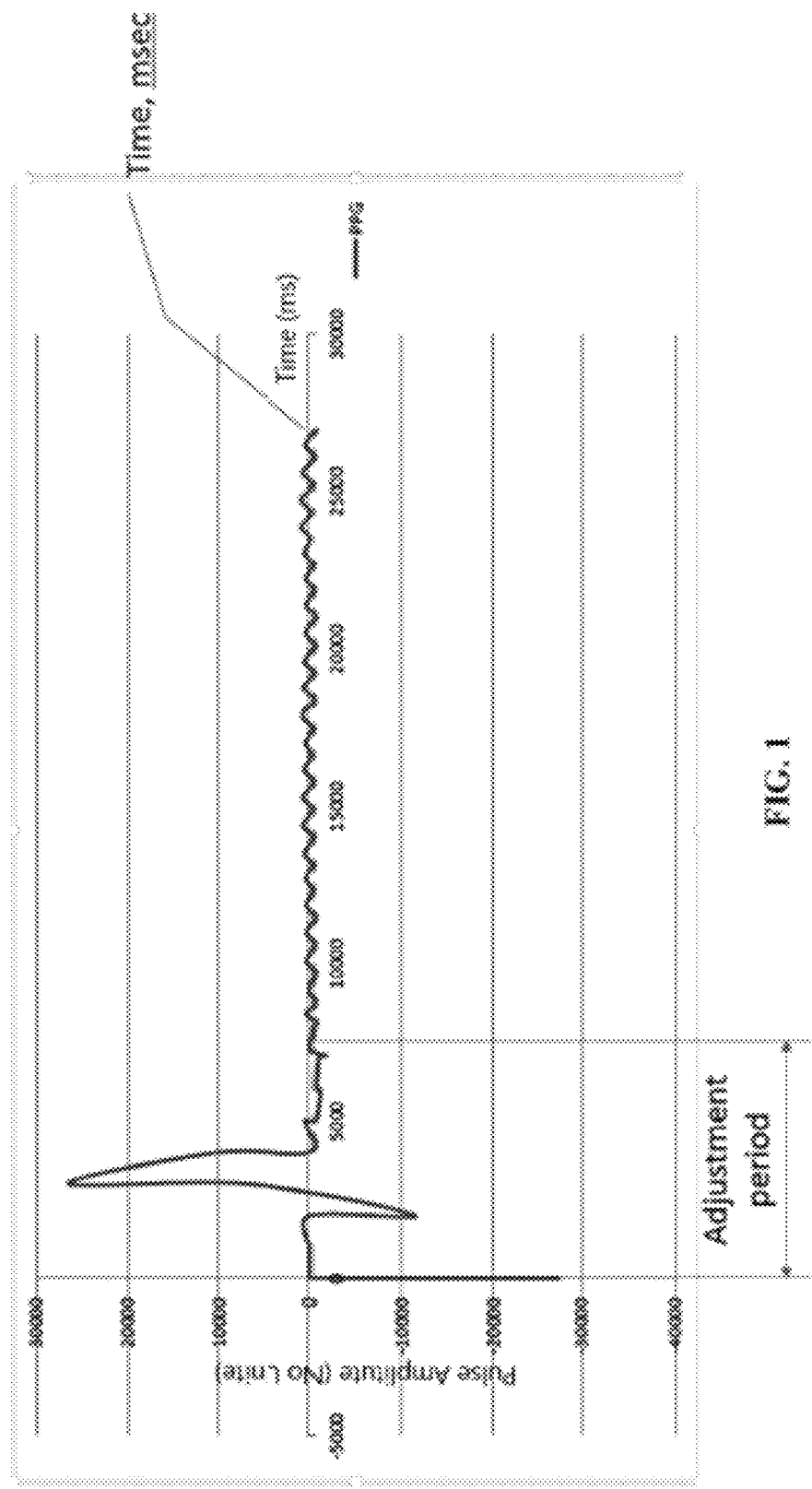
FIG. 1 is a graph that shows raw photoplethysmographic (PPG) measurements using the present invention.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not limit the invention, except as outlined in the claims.

The present invention includes a method of blood pressure estimation using trend analysis that includes a blood pressure trend computation comprising: a physical device equipped with a photoplethysmographic (PPG) sensor or magnetic sensor, a PPG/magnetic sensor utilizing a pulse oximeter for measuring changes in skin light absorption, wherein the physical device transmits results of the PPG/magnetic sensor measurements to a processing device, receiving the PPG/magnetic sensor measurements over a first time interval, identifying a second time interval within the first time interval with statistically stable measurements. In certain embodiments, the method includes further identifying within second time interval a sequence of time intervals containing an optimal number of systolic and diastolic cardiac periods (SCP, DCP) suitable for blood pressure (BP) trend computation, applying statistical analysis (e.g., chi-squared and goodness-of-fit) to determining the optimal sequence of time intervals, eliminating noise in the sequence of time intervals by applying a low-pass Fourier filter to each element of the sequence, computing trend of systolic blood pressure by finding slope of a best-fit line traversing systolic blood pressure measurement peaks, computing trend of diastolic blood pressure by finding slope of a best-fit line traversing diastolic blood pressure measurement troughs and inverting the slope sign, and combining trend analysis results to determine BP trend over a longer time period.

One example of an input/output device is a wireless communication is selected from at least one of: IEEE 802.11 (WiFi), IEEE 802.15.4, BLUETOOTH protocol, Near Field Communication (NFC), Radio Frequency Identification (RFID), SIGFOX protocol, WiMax (world interoperability for microwave access), Universal Mobile Telecommunications System (UMTS), 3GPP Long Term Evolution (LTE), IMS, High Speed Packet Access (HSPA), Global System for Mobile communication (GSM), 3G, 4G, 5G, 6G and higher, AM, or FM. Other examples for how the input/output device connects to a network can be selected from Zigbee, Bluetooth, WiMax (WiMAX Forum Protocol), Wi-Fi (Wi-Fi Alliance Protocol), GSM (Global System for Mobile Communication), PCS (Personal Communications Services protocol), D-AMPS (Digital-Advanced Mobile Phone Service Protocol), 6LoWPAN (IPv6 Over Low Power Wireless Personal Area Networks Protocol), ANT (ANT network protocol), ANT+, Z-Wave, DASH7 (DASH7 Alliance Protocol), EnOcean, INSTEON, NeuRF ON, Senceive, WirelessHART (Wireless Highway Addressable Remote Transducer Protocol), Contiki, TinyOS (Tiny OS Alliance Protocol), GPRS (General Packet Radio Service), TCP/IP (Transmission Control Protocol and Internet Protocol), CoAP (Constrained Application Protocol), MQTT (Message Queuing Telemetry Transport), TR-50 (Engineering Committee TR-50 Protocol, OMA LW M2M (Open Mobile Alliance LightWeight machine-to-machine Protocol), and ETSIM2M (European Telecommunication Standards Institute machine-to-machine Protocol), Bluetooth Low Energy (BLE), minimal energy Bluetooth signal, Infrared Data Association (IrDA) protocols, and standards related to any of the foregoing.

If the input/output device is connected physically to the apparatus via a Universal Serial Bus (USB) interface standard, a Compact Flash (CF) interface standard, a MultiMediaCard (MMC) interface standard, an embedded MMC (eMMC) interface standard, a Thunderbolt interface standard, a UFS interface standard, a Secure Digital (SD) interface standard, a Memory Stick interface standard, an xD-picture card interface standard, an Integrated Drive Electronics (IDE) interface standard, a Serial Advanced Technology Attachment (SATA) interface standard, an external SATA (eSATA) interface standard, a Small Computer System Interface (SCSI) interface standard, a Serial Attached Small Computer System Interface (SAS) interface standard, a Fiber Channel interface standard, an Ethernet interface standard, Peripheral Component Interconnect (PCI), Infiniband, or Firewire.

The present invention was compared and tested against existing method and devices by: taking blood pressure measurement using a standard methodology and starting photoplethysmographic (PPG) sensor measurement at the same time, using PPG measurements to compute trends of systolic and diastolic blood pressure change, and using initial blood pressure measurement and computed trends to determine blood pressure for the duration of PPG measurements.

Systolic and Diastolic cardiac period (SCP and DCP, respectively) values were used previously for computing blood pressure using a combination of a PPG and an electrocardiogram (ECG) device. A PPG method has not been used for BP trend measurement. Computation of optimal trend estimation intervals and application of a Fourier filter to the original data are shown herein.

For the computations herein, the present inventors used PPG measurements provided by a wearable device (a watch) connected by a BlueTooth link to a mobile phone powered by the Android OS. PPG measurements were recorded by an application and saved in a file on the mobile device. Saved files were later downloaded to a computer and analyzed using a proprietary software program.

PPG signal is noisy. FIG. 1 illustrates a typical PPG measurement over an interval of approximately 27 sec. As shown in FIG. 1, PPG measurement began at time 0. There is a significant instability in measurement immediately after the start point followed by an interval of more stable measurements suitable for BP trend computation, which is referred to as evaluation interval. The beginning of the evaluation interval is estimated by computing z-score value on a subinterval and comparing it with a z-score value computed on a previous subinterval.

A Z-score is a statistical measure in which the absolute value represents the distance between the raw score of a random variable, x, and the population mean, $\mu$, in units of the standard deviation, $\sigma$:

$$z = \frac{x - \mu}{\sigma}$$

In order to determine a point in time when PPG measurements have stabilized the inventors computed the distance between population mean of a previous subinterval and population mean of current subinterval:

$$\frac{\mu_2 - \mu_1}{\sigma_1} \text{ and } \frac{\mu_1 - \mu_2}{\sigma_2}$$

When the distance between two successive z-score computations becomes less than a preset noise tolerance level the inventors consider measurement process stable and select current subinterval as a starting subinterval of the BP trend estimation period.

For example, the duration of each stabilization subinterval depends on the measurement rate and is typically set at 1 sec. In these computations, the noise tolerance level was set at 0.1. A typical duration of the adjustment period shown in FIG. 1 is between 8 sec and 12 sec.

Figure 2:
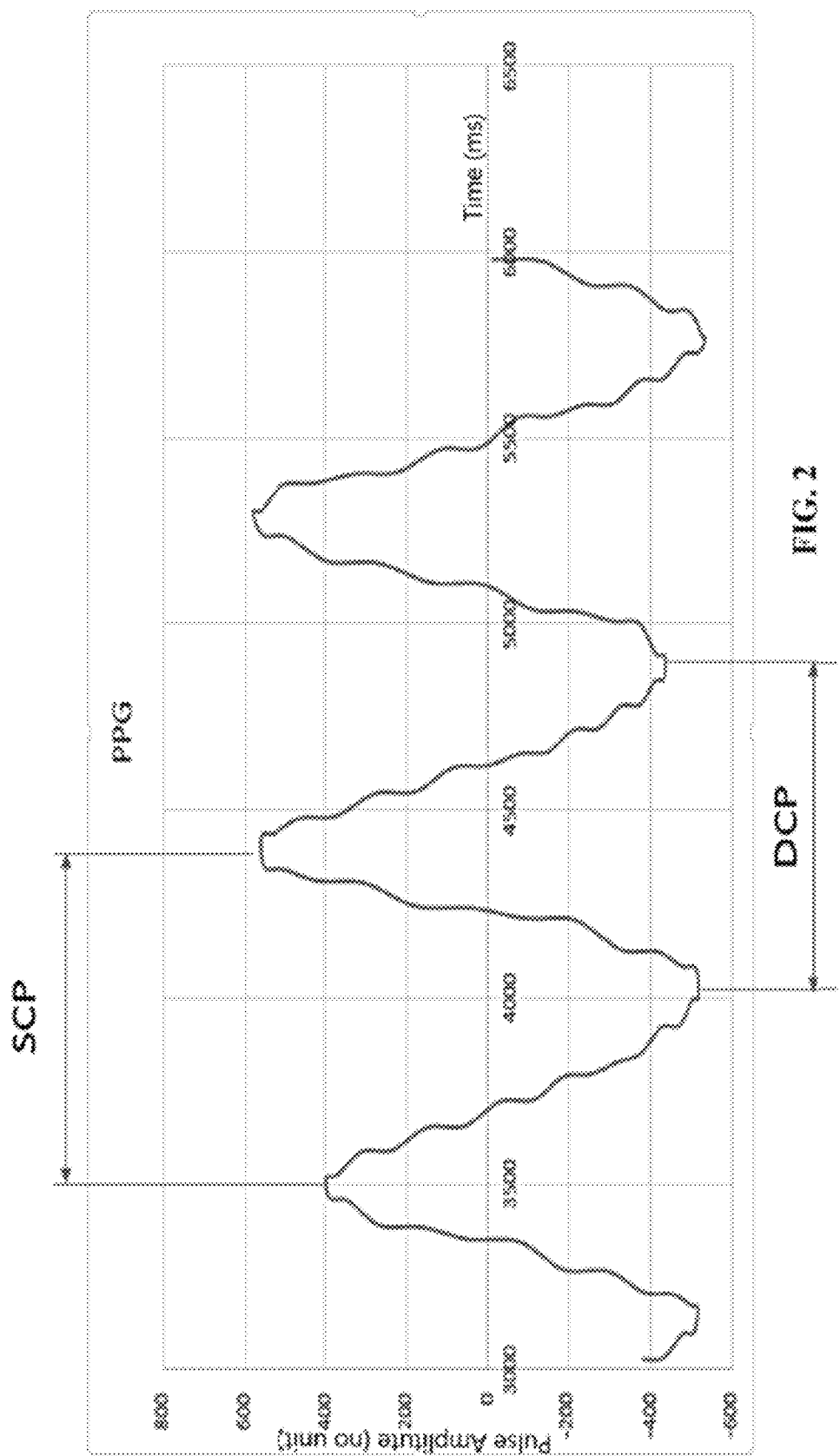
FIG. 2 is a graph that shows systolic and diastolic cardiac periods using the present invention.

Once the beginning of the interval of measurement stability has been computed a more cohesive pattern of the PPG signal is observed. FIG. 2 illustrates a pattern of the PPG signal on the interval of measurement stability.

It was found that, when PPG signal is being used the duration of the systolic cardiac period (SCP) and the diastolic cardiac period (DCP) provides a relative measure of blood pressure. Namely, the time interval between two PPG measurement peaks correspond to SCP and time interval between two PPG measurement troughs correspond to DCP. Shortening of SCP and DCP indicates an increase in blood pressure while longer SCP and DCP correspond to lower blood pressure. Thus, for estimating a trend in blood pressure measurements, the inventors measured the distance between successive local maxima and minima in PPG signal.

Figure 3:
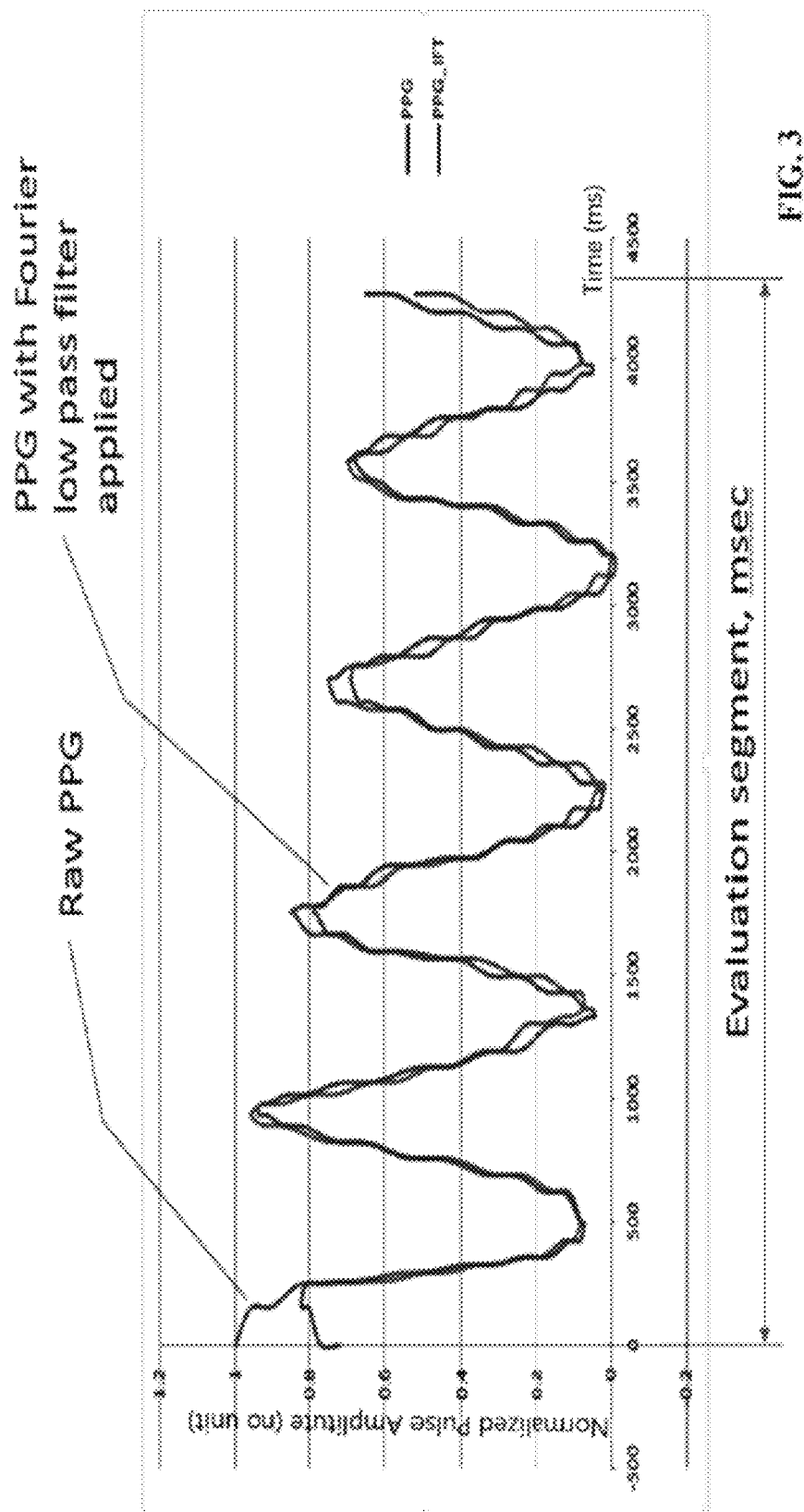
FIG. 3 is a graph that shows PPG measurements with applied Fourier filter using the present invention.

As one can see in FIG. 2, the PPG signal has extraneous noise. In order to make these computations more precise the inventors apply an adaptive or fixed low-pass Fourier filter, which eliminates high frequency signal in PPG measurements. The result from applying a low-pass Fourier filter is presented in FIG. 3. By applying a low-pass Fourier filter a significantly smoother representation was obtained, which enabled a more precise estimation of the local minima and maxima of the measured signal. For example, in order to find local extremes each potential point was bracketed using the Golden Section Search principle, combined with parabolic interpolation (Brent's method) and converge on the extreme value with a preset fractional precision. In these measurements, a fractional precision of 0.005 was used. It was noted that further increases in fractional precision (e.g. 0.001) only negligently improved the results while significantly increasing time of computation. However, other methods can be used for eliminate noise in the signal of the present invention.

Figure 4:
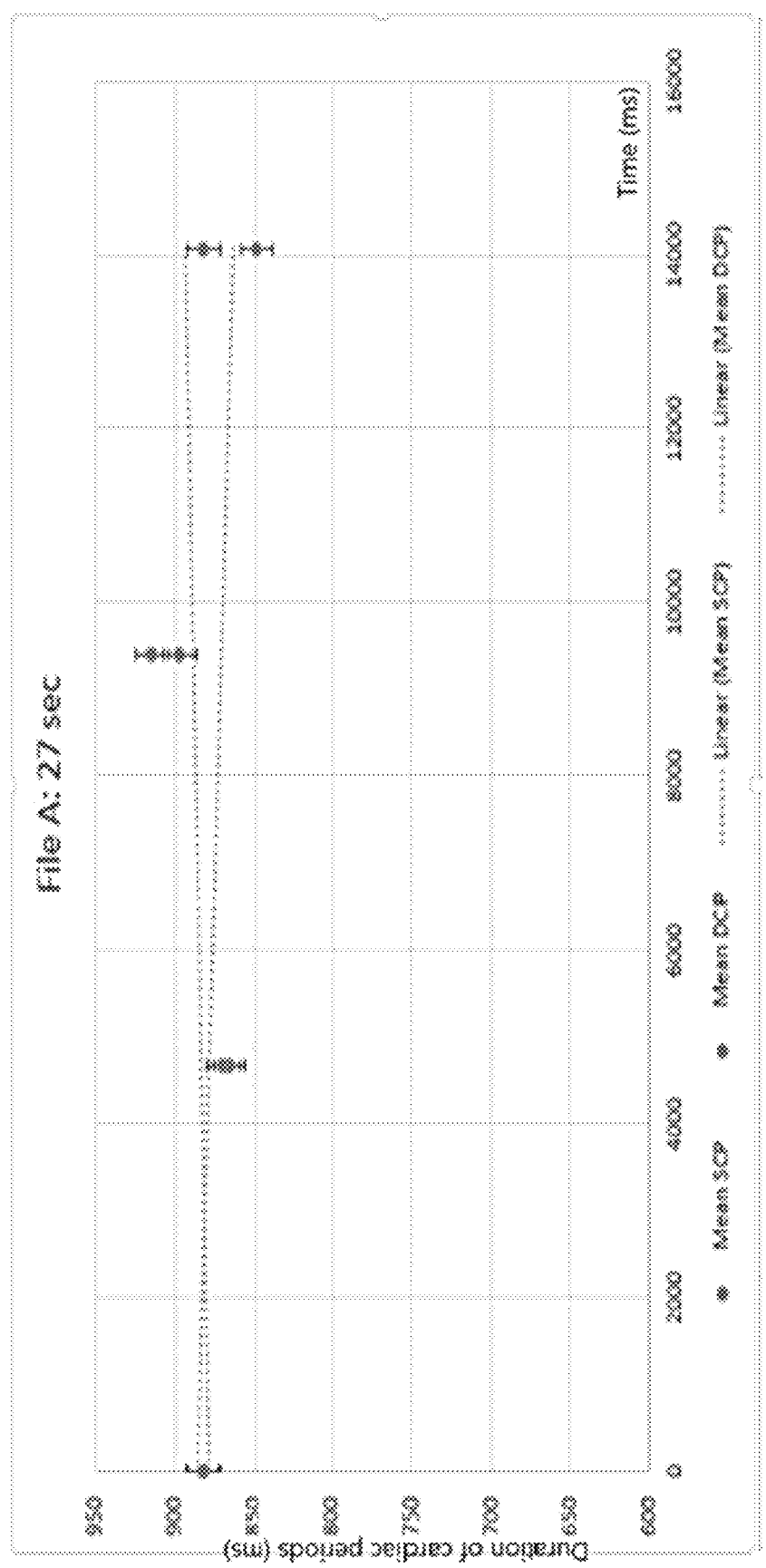
FIG. 4 is a graph that shows systolic and diastolic blood pressure trend computation using the present invention.

The time elapsed between computed local extreme measurements is a timeline of observed SCP and DCP values and their change in time. In a next step, a best-fit line was computed, which slope is an indicator of a trend in the blood pressure. This method of computing blood pressure trend is illustrated in FIG. 4. In FIG. 4, the x-axis represents elapsed time in the BP estimation period and the y-axis is the duration of the respective cardiac periods. Each measurement point is a mean SCP and DCP value on a corresponding estimation subinterval. The measurement points become a basis for calculating a best-fit line. Best-fit lines were computed using the minimal square distance method.

Since SCP and DCP are inverse indicators of change in the blood pressure, FIG. 4 indicates a slightly downward trend in diastolic blood pressure and a slightly upward trend in the systolic blood pressure.

The above methodology enables computing BP trend on a relatively short observation interval. It was found that, as an observation interval becomes more prolonged, additional noise is injected into PPG signal measurements. This phenomena of additional noise is illustrated in FIG. 5.

Figure 5:
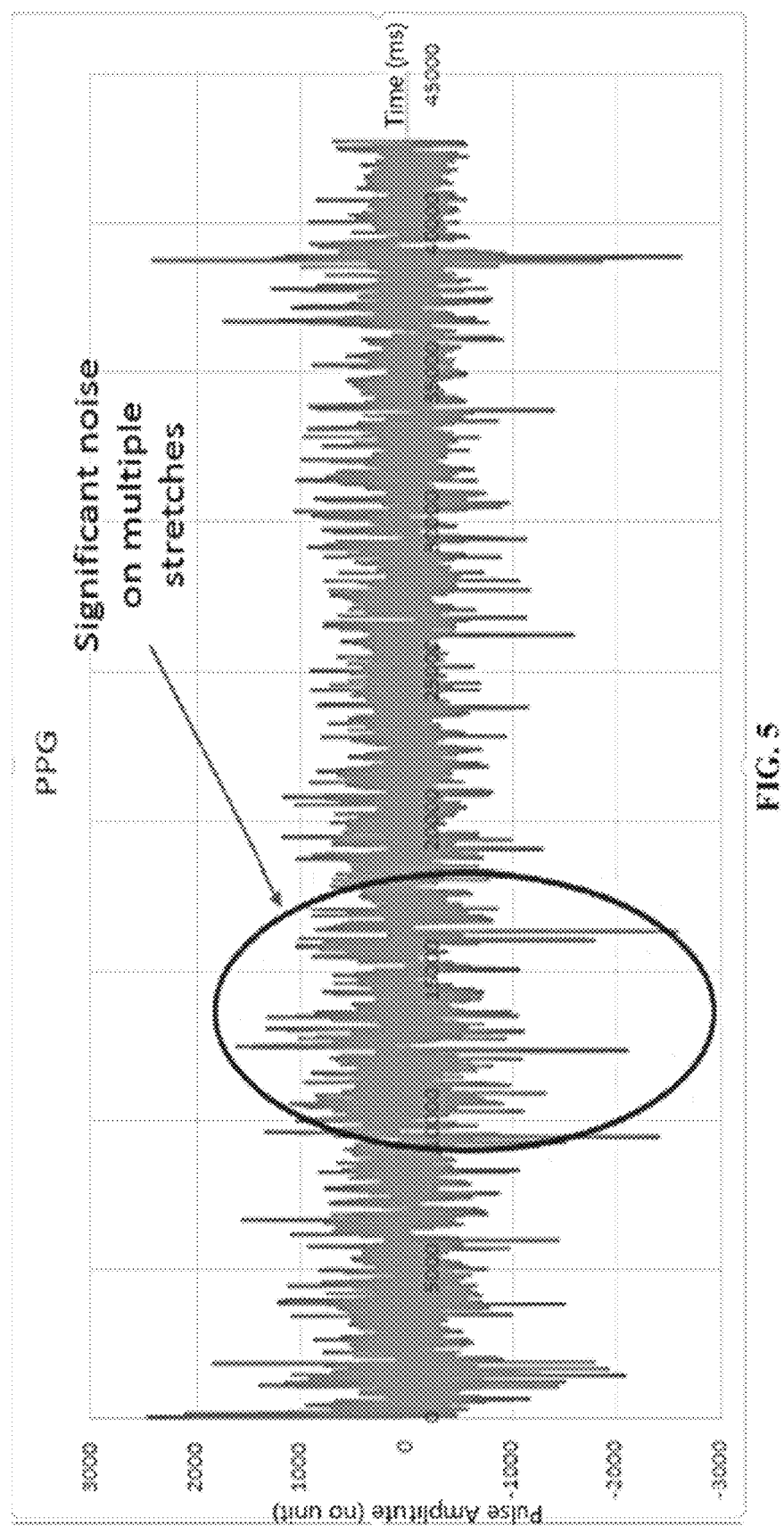
FIG. 5 is a graph that shows raw PPG signal measurements over a longer time interval using the present invention.

In this non-limiting example. the measurements shown in FIG. 5 span 1249 sec (note: x-axis is resealed). During this time a person wearing the device was engaged in multiple activities such as walking, working on a computer, changing position, etc. Since these activities affected the measurements BP trend computation on a longer interval requires identifying evaluation intervals on which PPG signal measurements are relatively stable.

An important part of evaluation intervals selection is a determination of an optimal length of such intervals. The inventors optimized evaluation intervals length based on the number of systolic peaks and diastolic troughs in the interval thus balancing estimation precision and the time required to determine the extreme PPG signal values.

When determining optimal evaluation interval length the inventors used Pearson chi-square goodness-of-fit test for measuring the quality of the observations approximation. A correctly computed model yields goodness-of-fit metric q=1. Other values of q indicate a poor model fit: either a deficiency in capturing the data or an excessive impact of the noise (over-fitting). A goodness-of-fit (GOF) criteria was computed for time intervals of a varying duration and an average number of systolic peaks and diastolic troughs observed on each evaluation interval duration. Then a trend line was computed for each evaluation interval duration and a $\chi 2$ statistic has been computed for both the systolic and the diastolic trend line. A smaller value of the statistic indicates a better approximation but this parameter is less important than the "goodness-of-fit" metric q. Thus, the present invention can also include a feedback and monitoring algorithm to ensure the GOF is >0.9. If the measurement results are unstable, then the algorithm is modified by changing the sampling rate, using a different correlation algorithm, using a different convergence monitoring (curve fitting the GOF convergence) longer integration time, repositioning the sensors, or moving to another area where possible spurious emissions are less, until the GOF is >0.9. Once calibrated, however, such changes would only be necessary if the evaluation is outside the computed model yields a GOF is <0.9. The skilled artisan will recognize that the GOF is >0.9 may vary by up to 25% on any given measurement and that an increase in sampling can reduce the variation over time. However, the present invention is able to very rapidly and consistently provide a final GOF is >0.9 in just 2, 3, 4, 5, 6, 7, 8, 10, 11, 15, 20, 25 or more cycles. Further, the device can be calibrated manually or automatically to take into consideration environmental conditions that could affect the measurement, thus eliminating those or mitigating their effect on a blood pressure calculation. For example, the device can take into account the present of certain electromagnetic radiations, vibration, ultrasound, or other radiations that can affect measurements, e.g., fluorescent lights or transformers that can add noise to very sensitive measurements.

An alarm should be provided at the central processing/monitoring unit and also displayed on the measuring wristband (or other body locations) device itself.

The results of this analysis are presented in Table 1. In Table 1, S-peaks denote systolic peaks and D-troughs denote diastolic troughs.

TABLE 1

Evaluation interval duration selection

| Evaluation interval, sec | Average number of S-peaks | Goodness-of-fit for S, q | Chi-square value, $S\chi^2$ | Average number of D-troughs | Goodness-of-fit for D, q | Chi-square value, $D\chi^2$ |
|---|---|---|---|---|---|---|
| 7 | 6.1 | 0 | 94.5 | 5.9 | 0 | 220.0 |
| 8 | 7.0 | 0.84 | 24.0 | 7.2 | 0.53 | 30.8 |
| 9 | 9.0 | 0.37 | 32.9 | 8.1 | 0.12 | 40.3 |
| 10 | 10.1 | 0.94 | 18.8 | 9.9 | 0.85 | 22.2 |
| 11 | 11.5 | 0.93 | 18.6 | 10.6 | 1.00 | 7.8 |
| 12 | 12.6 | 1.00 | 12.0 | 12.1 | 1.00 | 12.2 |
| 15 | 16.2 | 1.00 | 3.3 | 15.9 | 1.00 | 2.5 |
| 20 | 22.6 | 1.00 | 3.8 | 21.9 | 1.00 | 4.8 |

As one can see in Table 1, a 12 second long evaluation interval is an optimal selection, which satisfies the goodness-of-fit criteria and a minimal computational effort at that level of veracity. A 15 second long evaluation interval is also a good match for purposes of the present invention, but it is also possible to choose to minimize computation time over a better chi-square value and its possible to use a 12 second long evaluation interval in this model, while still maintaining high quality results.

Figure 6:
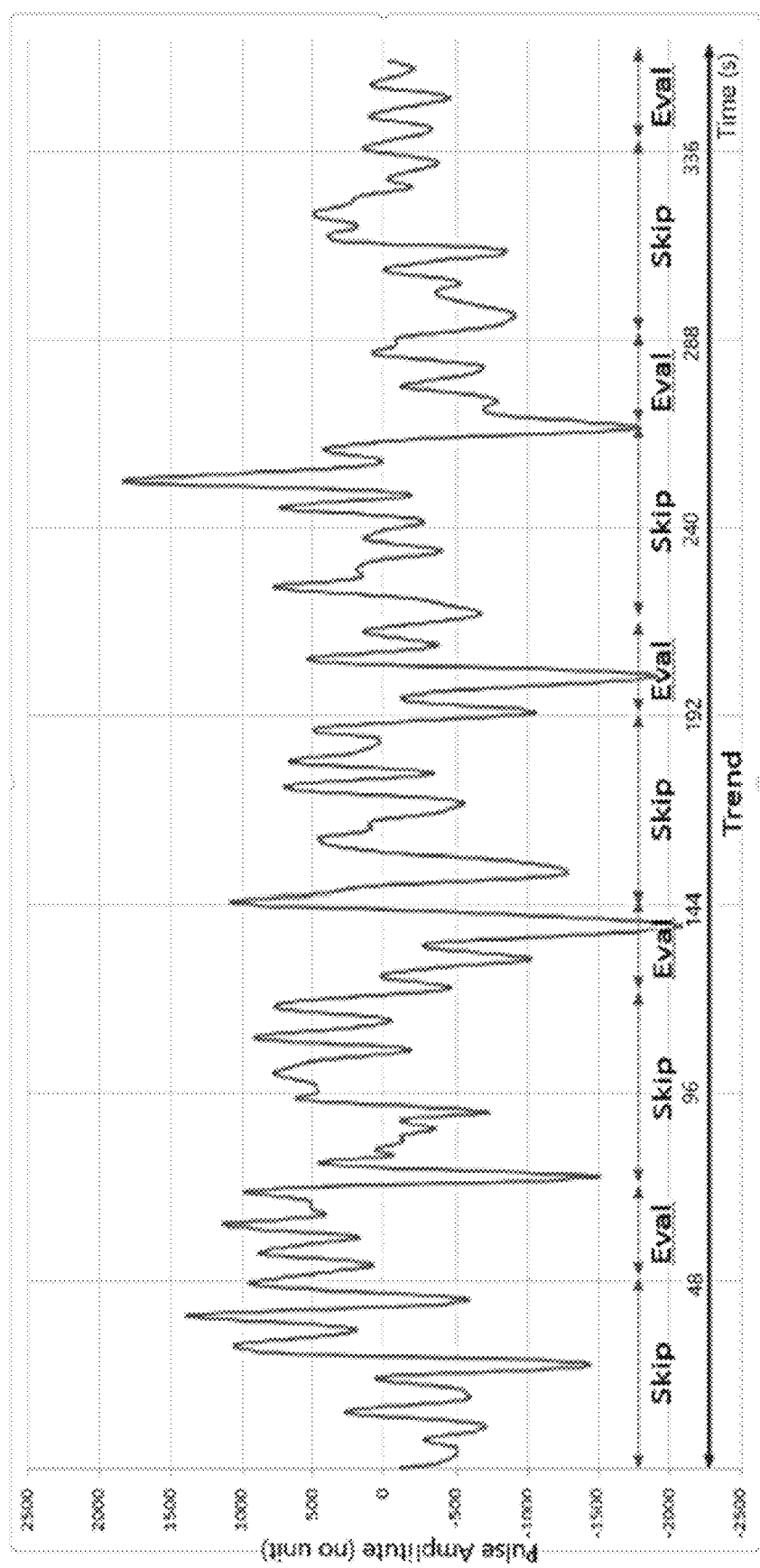
FIG. 6 is a graph that shows blood pressure trend computation on a segment using the present invention.

FIG. 6 shows the selection of BP trend evaluation intervals on a 420 second long PPG signal measurement interval. The inventors used 12 second evaluation intervals each followed by an interval during which no evaluation has been attempted. For this computation, the inventors selected a length for each "skip" interval to be 2.5 times the duration of the evaluation interval. Such selection allows us to create a representative population of samples along of the PPG signal measurement interval.

Figure 7:
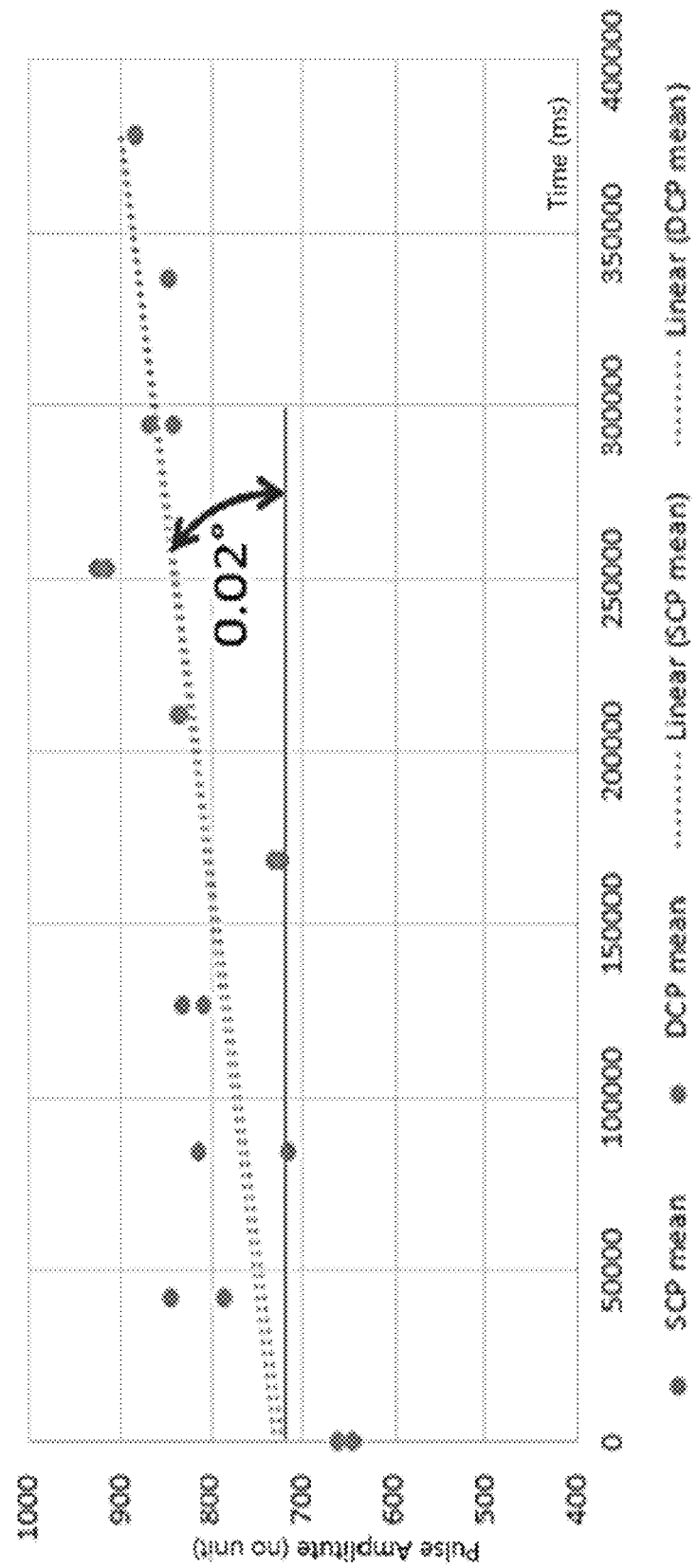
FIG. 7 is a graph that shows Blood pressure trend computation example using the present invention.

FIG. 7 shows an example of a BP trend calculation on a 7 min long PPG signal measurement interval. Keeping in mind that SCP and DCP duration is inverse to the blood pressure, it was possible to conclude that over this PPG signal measurement interval there was a slight decrease in both of the systolic and the diastolic blood pressure metrics.

In order to validate the approach to BP trend computation shown herein, the inventors measured the PPG signal for a prolonged period and made several check point blood pressure measurements using a standard blood pressure measurement technique (cuff). The results of comparative study are presented in FIG. 8.

Figure 8:
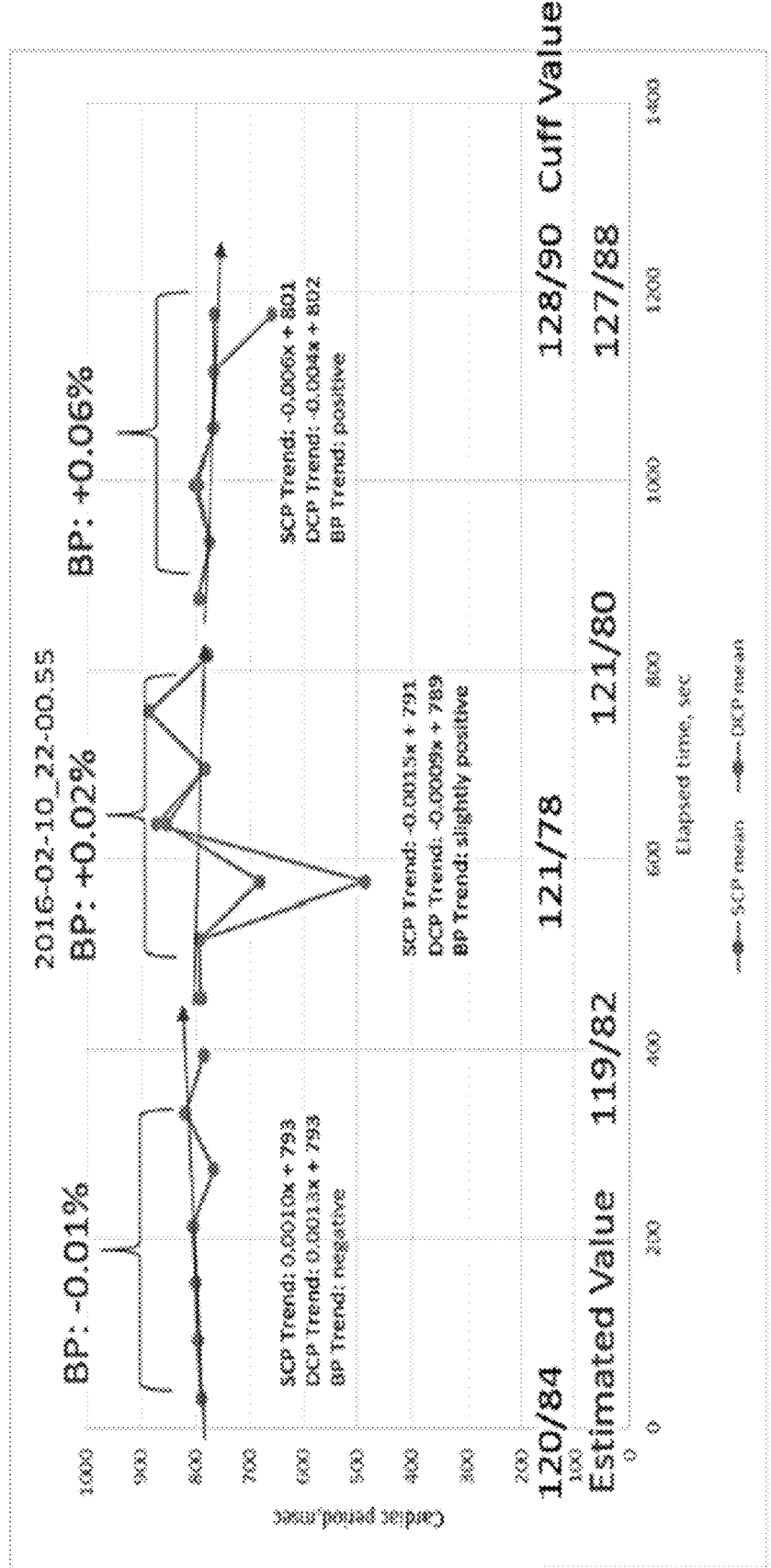
FIG. 8 is a graph that shows a comparative blood pressure measurement study using the present invention.

The blood pressure measurements shown in FIG. 8 were made at the beginning of the PPG signal measurement period, at a mid-point and at the end of that period. Blood pressure trends were estimated between the cuff measurement checkpoints. Blood pressure values based on the trend estimates were computed using only the first cuff measurement taken at time 0. Estimated blood pressure values at the subsequent checkpoints were calculated using the slope of a trend line on a respective measurement segment. A comparison between the cuff blood pressure measurements and blood pressure estimates obtained using the trend computation method shows that the estimated values are within 1% margin of the blood pressure measurements made using a standard stationary methodology.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), property(ies), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

What is claimed is:

1. An apparatus for blood pressure trend determination of a subject comprising:
  a housing;
  at least one of a photoplethysmographic (PPG) sensor or a magnetic sensor in or on the housing and adapted to be worn by the subject, wherein the PPG/magnetic sensor uses a pulse oximeter to measure changes in skin light absorption;
  a processor for receiving a signal from the at least one of the PPG sensor or the magnetic sensor measurements, wherein the processor comprises a non-transitory computer readable medium having instruction stored thereon, wherein the instructions, when executed by the processor, cause the processor to:
    receive the PPG/magnetic sensor measurements over a first time interval;
    identify a second time interval within the first time interval with statistically stable measurements, wherein the statistically stable measurement is obtained by computing a z-score value on a subinterval that is compared to a prior z-score value computed from a previous subinterval, wherein the z-score:

is a statistical measure in which an absolute value represents a distance between a raw score of a random variable, x, and a population mean, μ, in units of standard deviation, σ:

$$z = \frac{x - \mu}{\sigma}$$

and in order to compute a stabilized point in time when PPG measurements have stabilized, a distance between a population mean of a previous subinterval and a population mean of current subintervals is calculated as follows:

$$\frac{\mu_2 - \mu_1}{\sigma_1} \text{ and } \frac{\mu_1 - \mu_2}{\sigma_2}$$

wherein the PPG measurements have stabilized when a distance between two successive z-score computations becomes less than a preset noise tolerance level;
identify within the second time interval a sequence of time intervals containing a number of both systolic and diastolic cardiac periods (SCP, DCP) suitable for blood pressure trend computation, wherein the SCP are identified by calculating the time interval between PPG peaks and the DCP are identified by calculating the time interval between PPG troughs;
apply a statistical analysis to determining the sequence of time intervals;
eliminate a noise in the sequence of time intervals by applying an adaptive or fixed low-pass Fourier filter to each element of the sequence;
compute a trend of systolic blood pressure by finding a slope of a best-fit line to systolic cardiac period values over time;
compute a trend of diastolic blood pressure by finding a slope of a best-fit line to diastolic cardiac period values over time and inverting the slope sign; and
combine the trend analysis results to determine the blood pressure trend over a time period; and
an input/output device that at least one of stores, displays, or transmits blood pressure trend of the subject.

2. The apparatus of claim 1, wherein the processor receives blood pressure measurements obtained from using a pressure cuff and the PPG/magnetic sensor at the same time; and calibrates the PPG/magnetic sensor to match the pressure cuff measurements.

3. The apparatus of claim 1, wherein the processor further uses PPG measurements to compute trends of systolic and diastolic blood pressure change.

4. The apparatus of claim 1, wherein the processor further uses initial blood pressure measurement and computed trends to determine blood pressure for the duration of PPG measurements.

5. The apparatus of claim 1, wherein the statistical analysis is a chi-squared and a goodness-of-fit analysis.

6. The apparatus of claim 1, wherein the input/output protocol is selected from at least one of: IEEE 802.11 (WiFi), IEEE 802.15.4, BLUETOOTH protocol, Near Field Communication (NFC), Radio Frequency Identification (RFID), SIGFOX protocol, WiMax (world interoperability for microwave access), Universal Mobile Telecommunications System (UMTS), 3GPP Long Term Evolution (LTE), IMS, High Speed Packet Access (HSPA), Global System for Mobile communication (GSM), 3G, 4G, 5G, 6G and higher, AM, or FM.

7. The apparatus of claim 1, wherein the input/output device connects to a network selected from Zigbee, Bluetooth, WiMax (WiMAX Forum Protocol), Wi-Fi (Wi-Fi Alliance Protocol), GSM (Global System for Mobile Communication), PCS (Personal Communications Services protocol), D-AMPS (Digital-Advanced Mobile Phone Service Protocol), 6LoWPAN (IPv6 Over Low Power Wireless Personal Area Networks Protocol), ANT (ANT network protocol), ANT+, Z-Wave, DASH7 (DASH7 Alliance Protocol), EnOcean, INSTEON, NeuRF ON, Senceive, WirelessHART (Wireless Highway Addressable Remote Transducer Protocol), Contiki, TinyOS (Tiny OS Alliance Protocol), GPRS (General Packet Radio Service), TCP/IP (Transmission Control Protocol and Internet Protocol), CoAP (Constrained Application Protocol), MQTT (Message Queuing Telemetry Transport), TR-50 (Engineering Committee TR-50 Protocol, OMA LW M2M (Open Mobile Alliance LightWeight machine-to-machine Protocol), and ETSIM2M (European Telecommunication Standards Institute machine-to-machine Protocol), Bluetooth Low Energy (BLE), minimal energy Bluetooth signal, Infrared Data Association (IrDA) protocols, and standards related to any of the foregoing.

8. The apparatus of claim 1, wherein the input/output device is connected physically to the apparatus via a Universal Serial Bus (USB) interface standard, a Compact Flash (CF) interface standard, a MultiMediaCard (MMC) interface standard, an embedded MMC (eMMC) interface standard, a Thunderbolt interface standard, a UFS interface standard, a Secure Digital (SD) interface standard, a Memory Stick interface standard, an xD-picture card interface standard, an Integrated Drive Electronics (IDE) interface standard, a Serial Advanced Technology Attachment (SATA) interface standard, an external SATA (eSATA) interface standard, a Small Computer System Interface (SCSI) interface standard, a Serial Attached Small Computer System Interface (SAS) interface standard, a Fibre Channel interface standard, an Ethernet interface standard, Peripheral Component Interconnect (PCI), Infiniband, or Firewire.

9. The apparatus of claim 1, wherein the input/output device communicates with a local network that is connected to a global telecommunications network to store or transmit information through the cloud.

10. The apparatus of claim 1, wherein the magnetic sensor detects pulse induced body movement that affects the magnetic field to measure a blood flow.

11. The apparatus of claim 1, wherein an output from the magnetic sensor is used to determine a magnetocardiogram (MCG) and a cardiac cycle.

12. The apparatus of claim 1, wherein the processor further calculates an absolute blood pressure locally at the magnetic sensor.

13. The apparatus of claim 1, wherein the processor distinguishes between the magnetic field caused by the blood flow and a skin movement that disturbs the electromagnetic field or correlates skin movement to blood flow.

14. The apparatus of claim 1, wherein the processor further comprises a feedback and monitoring algorithm that calculates that a goodness-of-fit (GOF) is >0.9.

15. A method of blood pressure trend determination of a subject comprising:

providing a device comprising at least one of a photoplethysmographic (PPG) sensor or a magnetic sensor to the subject, wherein the PPG/magnetic sensor uses a pulse oximeter to measure changes in skin light absorption;

transmitting results of the PPG/magnetic sensor measurements to a processor, wherein the processor comprises a non-transitory computer readable medium having instruction stored thereon, wherein the instructions, when executed by the processor, cause the processor to:
receive the PPG/magnetic sensor measurements over a first time interval;
identify a second time interval within the first time interval with statistically stable measurements, wherein the statistically stable measurement is obtained by computing a z-score value on a subinterval that is compared to a prior z-score value computed from a previous subinterval, wherein the z-score:

is a statistical measure in which an absolute value represents a distance between a raw score of a random variable, x, and a population mean, μ, in units of standard deviation, σ:

$$z = \frac{x-\mu}{\sigma}$$

and in order to compute a stabilized point in time when PPG measurements have stabilized, a distance between a population mean of a previous subinterval and a population mean of current subintervals is calculated as follows:

$$\frac{\mu_2 - \mu_1}{\sigma_1} \text{ and } \frac{\mu_1 - \mu_2}{\sigma_2}$$

wherein the PPG measurements have stabilized when a distance between two successive z-score computations becomes less than a preset noise tolerance level;
identify within the second time interval a sequence of time intervals containing a number of both systolic and diastolic cardiac periods (SCP, DCP) suitable for blood pressure trend computation, wherein the SCP are identified by calculating the time interval between PPG peaks and the DCP are identified by calculating the time interval between PPG troughs;
apply a statistical analysis to determining the sequence of time intervals;
eliminate a noise in the sequence of time intervals by applying an adaptive or fixed low-pass Fourier filter to each element of the sequence;
compute a trend of systolic blood pressure by finding a slope of a best-fit line to systolic cardiac period values over time;
compute a trend of diastolic blood pressure by finding a slope of a best-fit line to diastolic cardiac period values over time and inverting the slope sign; and
combine the trend analysis results to determine the blood pressure trend over a time period; and
providing an input/output device that at least one of stores, displays, or transmits blood pressure trend of the subject.

16. The method of claim 15, further comprising taking blood pressure measurement using a standard methodology and starting PPG sensor measurement at the same time.

17. The method of claim 15, further comprising using PPG measurements to compute trends of systolic and diastolic blood pressure change.

18. The method of claim 15, further comprising using initial blood pressure measurement and computed trends to determine blood pressure for the duration of PPG measurements.

19. The method of claim 15, further comprising using a statistical analysis that is a chi-squared and a goodness-of-fit analysis.

20. The method of claim 15, wherein the input/output protocol is selected from at least one of: IEEE 802.11 (WiFi), IEEE 802.15.4, BLUETOOTH protocol, Near Field Communication (NFC), Radio Frequency Identification (RFID), SIGFOX protocol, WiMax (world interoperability for microwave access), Universal Mobile Telecommunications System (UMTS), 3GPP Long Term Evolution (LTE), IMS, High Speed Packet Access (HSPA), Global System for Mobile communication (GSM), 3G, 4G, 5G, 6G and higher, AM, or FM.

21. The method of claim 15, wherein the input/output device connects to a network selected from Zigbee, Bluetooth, WiMax (WiMAX Forum Protocol), Wi-Fi (Wi-Fi Alliance Protocol), GSM (Global System for Mobile Communication), PCS (Personal Communications Services protocol), D-AMPS (Digital-Advanced Mobile Phone Service Protocol), 6LoWPAN (IPv6 Over Low Power Wireless Personal Area Networks Protocol), ANT (ANT network protocol), ANT+, Z-Wave, DASH7 (DASH7 Alliance Protocol), EnOcean, INSTEON, NeuRF ON, Senceive, WirelessHART (Wireless Highway Addressable Remote Transducer Protocol), Contiki, TinyOS (Tiny OS Alliance Protocol), GPRS (General Packet Radio Service), TCP/IP (Transmission Control Protocol and Internet Protocol), CoAP (Constrained Application Protocol), MQTT (Message Queuing Telemetry Transport), TR-50 (Engineering Committee TR-50 Protocol, OMA LW M2M (Open Mobile Alliance LightWeight machine-to-machine Protocol), and ETSIM2M (European Telecommunication Standards Institute machine-to-machine Protocol), Bluetooth Low Energy (BLE), minimal energy Bluetooth signal, Infrared Data Association (IrDA) protocols, and standards related to any of the foregoing.

22. The method of claim 15, wherein the input/output device is connected physically to the apparatus via a Universal Serial Bus (USB) interface standard, a Compact Flash (CF) interface standard, a MultiMediaCard (MMC) interface standard, an embedded MMC (eMMC) interface standard, a Thunderbolt interface standard, a UFS interface standard, a Secure Digital (SD) interface standard, a Memory Stick interface standard, an xD-picture card interface standard, an Integrated Drive Electronics (IDE) interface standard, a Serial Advanced Technology Attachment (SATA) interface standard, an external SATA (eSATA) interface standard, a Small Computer System Interface (SCSI) interface standard, a Serial Attached Small Computer System Interface (SAS) interface standard, a Fibre Channel interface standard, an Ethernet interface standard, Peripheral Component Interconnect (PCI), Infiniband, or Firewire.

23. The method of claim 15, wherein the input/output device communicates with a local network that is connected to a global telecommunications network to store or transmit information through the cloud.

24. The method of claim 15, wherein the magnetic detector detects pulse induced body movement that affects the magnetic field to measure a blood flow.

25. The method of claim 15, wherein an output from the magnetic sensor is used to determine a magnetocardiogram (MCG) and a cardiac cycle.

26. The method of claim 15, wherein the processor further calculates an absolute blood pressure locally at the magnetic sensor.

27. The method of claim 15, wherein the processor distinguishes between the magnetic field caused by the blood flow and a skin movement that disturbs the electromagnetic field or correlates skin movement to blood flow.

28. The method of claim 15, further comprising a feedback and monitoring algorithm that calculates that a goodness-of-fit (GOF) is >0.9.

29. A computer implemented method for obtaining a blood pressure trend from a subject, comprising:
- providing a device comprising at least one of a photoplethismographic (PPG) sensor or a magnetic sensor to the subject, wherein the PPG/magnetic sensor uses a pulse oximeter to measure changes in skin light absorption;
- transmitting results of the PPG magnetic sensor measurements to a processor, wherein the processor comprises A non-transitory computer readable medium having instruction stored thereon, wherein the instructions, when executed by the processor, cause the processor to:
- receive the PPG/magnetic sensor measurements over a first time interval;
  - identify a second time interval within the first time interval with statistically stable measurements, wherein the statistically stable measurement is obtained by computing a z-score value on a subinterval that is compared to a prior z-score value computed from a previous subinterval, wherein the z-score:
- is a statistical measure in which an absolute value represents a distance between a raw score of a random variable, x, and a population mean, µ, in units of standard deviation, σ:

$$z = \frac{x-\mu}{\sigma}$$

and in order to compute a stabilized point in time when PPG measurements have stabilized, a distance between a population mean of a previous subinterval and a population mean of current subintervals is calculated as follows:

$$\frac{\mu_2 - \mu_1}{\sigma_1} \text{ and } \frac{\mu_1 - \mu_2}{\sigma_2}$$

wherein the PPG measurements have stabilized when a distance between two successive z-score computations becomes less than a preset noise tolerance level;
identify within the second time interval a sequence of time intervals containing a number of both systolic and diastolic cardiac periods (SCP, DCP) suitable for blood pressure trend computation, wherein the SCP are identified by calculating the time interval between PPG peaks and the DCP are identified by calculating the time interval between PPG troughs;
apply a statistical analysis to determining the sequence of time intervals;
eliminate a noise in the sequence of time intervals by applying an adaptive or fixed low-pass Fourier filter to each element of the sequence;
compute a trend of systolic blood pressure by finding a slope of a best-fit line to systolic cardiac period values over time traversing;
compute a trend of diastolic blood pressure by finding a slope of a best-fit line to diastolic cardiac period values over time and inverting the slope sign; and
combine the trend analysis results to determine the blood pressure trend over a time period.

30. A non-transitory computer readable medium for obtaining a blood pressure trend from a subject having instruction stored thereon, wherein the instructions, when executed by the processor, cause the processor to:
receive the PPG/magnetic sensor measurements over a first time interval;
identify a second time interval within the first time interval with statistically stable measurements, wherein the statistically stable measurement is obtained by computing a z-score value on a subinterval that is compared to a prior z-score value computed from a previous subinterval, wherein the z-score:
is a statistical measure in which an absolute value represents a distance between a raw score of a random variable, x, and a population mean µ, in units of standard deviation, σ:

$$z = \frac{x-\mu}{\sigma}$$

and in order to compute a stabilized point in time when PPG measurements have stabilized, a distance between a population mean of a previous subinterval and a population mean of current subintervals is calculated as follows:

$$\frac{\mu_2 - \mu_1}{\sigma_1} \text{ and } \frac{\mu_1 - \mu_2}{\sigma_2}$$

wherein the PPG measurements have stabilized when a distance between two successive z-score computations becomes less than a preset noise tolerance level;
identify within the second time interval a sequence of time intervals containing a number of both systolic and diastolic cardiac periods (SCP, DCP) suitable for blood pressure trend computation, wherein the SCP are identified by calculating the time interval between PPG peaks and the DCP are identified by calculating the time interval between PPG troughs;
apply a statistical analysis to determining the sequence of time intervals;
eliminate a noise in the sequence of time intervals by applying a low-pass Fourier filter to each element of the sequence;
compute a trend of systolic blood pressure by finding a slope of a best-fit line to systolic and diastolic cardiac period values over time;
compute a trend of diastolic blood pressure by finding a slope of a best-fit line to diastolic cardiac period values over time and inverting the slope sign; and
combine the trend analysis results to determine the blood pressure trend over a time period.

* * * * *